United States Patent [19]

Schnitzer et al.

[11] Patent Number: 5,692,497
[45] Date of Patent: Dec. 2, 1997

[54] MICROPROCESSOR-CONTROLLED VENTILATOR SYSTEM AND METHODS

[75] Inventors: Jay J. Schnitzer, Boston; John E. Thompson, Franklin, both of Mass.

[73] Assignees: Children's Medical Center Corporation; The General Hospital Corporation, both of Boston, Mass.

[21] Appl. No.: 649,068

[22] Filed: May 16, 1996

[51] Int. Cl.$^6$ .................................................. A61M 16/00
[52] U.S. Cl. .......................... 128/204.21; 128/204.18; 128/204.22; 128/204.23; 128/207.14
[58] Field of Search .................. 128/204.18, 204.21, 128/204.22, 204.23, 205.11, 205.23, 205.24, 201.14, 201.18

[56] References Cited

U.S. PATENT DOCUMENTS

| | | | |
|---|---|---|---|
| 3,460,541 | 8/1969 | Doherty | 128/207.14 |
| 3,538,918 | 11/1970 | Engelsher et al. | 128/207.14 |
| 3,599,642 | 8/1971 | Tindel | 128/207.14 |
| 3,682,166 | 8/1972 | Jacobs . | |
| 3,788,326 | 1/1974 | Jacobs | 128/207.14 |
| 3,910,270 | 10/1975 | Stewart | 128/203.24 |
| 3,983,879 | 10/1976 | Todd . | |
| 4,020,849 | 5/1977 | Jackson . | |
| 4,082,093 | 4/1978 | Fry et al. . | |
| 4,141,356 | 2/1979 | Smargiassi . | |
| 4,202,330 | 5/1980 | Jariabka | 128/204.18 |
| 4,224,939 | 9/1980 | Lang | 128/205.13 |
| 4,232,667 | 11/1980 | Chalon et al. | 128/203.26 |
| 4,421,113 | 12/1983 | Gedeon et al. | 128/204.23 |
| 4,502,482 | 3/1985 | DeLuccia et al. | 128/207.15 |
| 4,508,117 | 4/1985 | Rodari | 128/204.21 |
| 4,519,388 | 5/1985 | Schwanbom | 128/204.25 |
| 4,565,194 | 1/1986 | Weerda et al. | 128/204.23 |
| 4,593,690 | 6/1986 | Sheridan et al. | 128/207.15 |
| 4,652,258 | 3/1987 | Drach | 604/53 |
| 4,682,010 | 7/1987 | Drapeau et al. | 128/204.17 |
| 4,716,896 | 1/1988 | Ackerman | 128/250.26 |
| 4,773,411 | 9/1988 | Downs | 128/204.18 |
| 4,805,982 | 2/1989 | Tomoyori et al. | 350/96.24 |
| 4,850,349 | 7/1989 | Farahany | 128/207.15 |
| 4,892,095 | 1/1990 | Nakhgevany | 128/207.14 |
| 4,986,268 | 1/1991 | Tehrani | 128/204.22 |
| 4,996,980 | 3/1991 | Frankenberger et al. | 128/250.24 |
| 5,069,220 | 12/1991 | Casparie et al. | 128/719 |

(List continued on next page.)

FOREIGN PATENT DOCUMENTS

| | | | |
|---|---|---|---|
| 8801323 | 12/1989 | Netherlands | A61M 16/00 |
| 2 137 506 | 10/1984 | United Kingdom | A61M 16/00 |
| WO 89/02761 | 4/1989 | WIPO | A61M 16/00 |

OTHER PUBLICATIONS

Kolobow et al. (1994) *Anesth. Analg.* 78:455–461.
Raszynski et al. (1993) *ASAIO Journal* pp. M681–M685.
Mueller et al (1993) *Pediatric Research* 34:606–610.
Wilson et al. (1993) *Journal of Pediatric Surgery* 28:484–487.
Ingram *Adult Respiratory Distress Syndrome Part Eight Disorders of the Respiratory System* pp. 1240–1243.
Igenito *Mechanical Ventilatory Support Part Eight Disorders of the Respiratory System* pp. 1244–1247.

*Primary Examiner*—Vincent Millin
*Assistant Examiner*—V. Srivastava
*Attorney, Agent, or Firm*—Lappin & Kusmer LLP

[57] ABSTRACT

A microprocessor controlled ventilator controls a patient's breathing selectively. In a preferred aspect, the ventilator utilizes intratracheal pulmonary ventilation and a reverse thrust catheter to provide all patient inspiration. The microprocessor connects to a pneumatic subsystem which includes a variety of sensors and actuators and the catheter disposed in the patient's trachea. A feedback control loop provides a basis for controlling selected actuators within the subsystem to control the patient's breathing. The microprocessor provides the selective venting of expiration gases, and the selective mixing of treatment gases, such as anesthesia. The ventilator has a plurality of possible ventilating modes, each selectable by the user, thereby reducing the number of hospital equipment needed to all forms of ventilation required by a patients.

35 Claims, 6 Drawing Sheets

U.S. PATENT DOCUMENTS

| | | | |
|---|---|---|---|
| 5,072,726 | 12/1991 | Mazloomdoost et al. | 128/250.14 |
| 5,107,831 | 4/1992 | Halpern et al. | 128/204.21 |
| 5,129,390 | 7/1992 | Chopin et al. | 128/204.23 |
| 5,186,167 | 2/1993 | Kolobow | 128/207.14 |
| 5,237,987 | 8/1993 | Anderson et al. | 128/204.18 |
| 5,255,675 | 10/1993 | Kolobow | 128/204.18 |
| 5,303,698 | 4/1994 | Tobia et al. | 128/204.21 |
| 5,398,676 | 3/1995 | Press et al. | 128/204.23 |
| 5,400,777 | 3/1995 | Olsson et al. | 128/204.18 |
| 5,429,123 | 7/1995 | Shaffer et al. | 128/204.23 |
| 5,452,714 | 9/1995 | Anderson et al. | 128/205.11 |
| 5,494,068 | 2/1996 | De Vries et al. | 128/205.24 |
| 5,540,220 | 7/1996 | Gropper et al. | 128/204.23 |

MICROPROCESSOR-CONTROLLED VENTILATOR SYSTEM AND METHODS

BACKGROUND

Conventional mechanical ventilation ("CMV") has an important role in modern medicine by supporting patients with respiratory failure through external mechanical support. Respiratory failure comes, for example, from pulmonary conditions such as edema, hemorrhaging and respiratory distress; and can result from disease states such as neuromuscular diseases, myopathies, restrictive lung disease and asthma. The prior art mechanical ventilator replaces the patient's normal inspiration by injecting oxygen and humidified gas into the patient's airway in a manner that is physiologically compatible with the pressurization, volume, and time pattern of the patient's lungs. After inspiration, the ventilator circuitry opens a valve to vent the patient's airway to ambient pressure so that expiration naturally occurs through the relaxation of the patient's lungs and chest wall.

Several modes control the prior art ventilator, specifying the manner in which ventilator "breaths" are initiated, or "triggered," and cycled and limited. By way of example, a timer can provide the trigger signal and appropriate cycling, while a pressure sensor indicating maximum lung volume or air pressure can provide a safety limiter by activating the valve to ambient pressure upon the occurrence an overpressure event.

Nevertheless, the use of conventional ventilators in certain areas, such as in conjunction with a neonatal intensive care unit ("ICU"), has shown limitations in safety and efficacy. These ventilators are, for example, particularly prone to cause iatrogenic injury to fragile newborn lungs, and especially to lungs with pre-existing pathology or prematurity. In addition, acute and chronic complications related to barotrauma remain frequent, proving that high airway pressures increase the likelihood of pulmonary damage.

Some of the problems of the above-described mechanical ventilators have been reduced through intratracheal ventilation and intratracheal pulmonary ventilation ("ITPV"), such as described in connection with the reverse thrust catheter apparatus of U.S. Pat. Nos. 5,255,675 and 5,186,167 by Kolobow. ITPV utilizes a reverse thrust catheter ("RTC") that is positioned near the distal tip of an endotracheal tube in the patient's trachea and at the carina. The RTC supplies a continuous flow of humidified gas, including fresh oxygen, and flushes anatomical dead space within the trachea. The reverse thrust catheter generally includes a relatively small tube having a porous (i.e. diffuser) tip disposed within a cup-shaped deflector that diverts gas from the tip away from the direction of the carina and away from the walls of the trachea. In the prior art, catheters for ITPV are positioned in the patient's trachea to bypass the trachea's dead space so that the proximal trachea is utilized only for expiration. A timed expiratory valve reduces the pressures and oxygen flow rates for respiratory rates of 10 to 120 breaths per minute or higher. The catheter has a diffuser tip, and the patient is ventilated at a flow rate between 0.54 to 4.0 times the anatomical dead space per breath. The tip creates sub-atmospheric pressures near the carina and controls intratracheal pressures during the entire respiratory cycle to prevent over inflation of the lungs.

The following patents and articles provide useful background to the invention and are, accordingly, incorporated herein by reference: U.S. Pat. No. 5,255,675 by Kolobow, issued on Oct. 26, 1993, and entitled "Device for intratracheal ventilation and intratracheal pulmonary ventilation;" U.S. Pat. No. 5,186,167 by Kolobow, issued on Feb. 16, 1993, and entitled "Catheter tip for intratracheal ventilation and intratracheal pulmonary ventilation;" and Kolobow et al., *Intratracheal Pulmonary Ventilation (ITPV): Control of Positive End-Expiratory Pressure at the Level of the Carina Through the Use of a Novel ITPV Catheter Design*, Anesth Analg, V. 78, pp. 455–461 (1994).

Large animal studies utilizing the RTC have shown (i) that ITPV facilitates gas exchange at low peak pressures by a reduction in the anatomic dead space, (ii) that ITPV provides an enhanced exhalation and ventilation of small lungs, and (iii) that ITPV enhances blood $CO_2$ reduction while maintaining low airway pressures. However, in connection with certain treatments, such as the ventilating treatment of infants with a congenital diaphragmatic hernia ("CDH"), it is clear that the ITPV catheter has certain limitations associated with safety and reliability. Further, prior art ITPV adversely limits the available range of respiratory rates as well as the inspiratory-to-expiratory ("I:E") ratio.

Use of the RTC with prior art ventilators is also difficult and unwieldy, requiring, at times, over five separate pieces of equipment for various and standard operative uses. Accordingly, the ergonomics associated with using the ITPV catheter are oftentimes cumbersome.

It is, accordingly, an object of the invention to provide an ITPV-specific ventilator. Another object of the invention is to provide a flexible pediatric ventilator with ITPV capability. Yet another object of the invention is to provide methodology for increased control of pulmonary ventilation, such as ventilation with nitric oxide administration, high frequency ventilation and anesthesia. Still another object of the invention is to provide portable and transportable pulmonary ventilating apparatus with multi-mode support of patients in intensive care. Another object of the invention is to provide an improved mechanical ventilator that has adequate ventilation at reduced airway pressures, particularly in a premature model. These and other objects will become apparent in the description which follows.

SUMMARY OF THE INVENTION

In one aspect, the invention provides a method of controlling ITPV. During ventilation, a microprocessor and connected flow sensors monitor the inspiratory and expiratory flow rates. Thereafter, the microprocessor controls the timing of the exhalation valve as preset by the operator, providing ventilation with two alternative modes: the first mode is to lower the arterial $PaCO_2$ at the same airway pressure; and the second mode is to maintain the same $PaCO_2$ at lower airway pressures.

The step of monitoring can include the step of monitoring the flow rates with a flow rate sensor connected to the microprocessor. Similarly, the step of controlling the flow rates can include the step of regulating the flow rate from the microprocessor in response to a signal generated by a flow rate sensor connected in fluid communication with the patient. In a preferred aspect, the microprocessor regulates the energy applied to a coil of a solenoid to actuate a mechanical valve, thereby controlling the flow rate through an associated conduit, e.g., the tubing or catheter connected in fluid communication with the patient's inspiratory and/or expiratory breathing.

In other aspects, flow rate sensors, e.g., pneumotachs, are connected to sense the inspiratory and/or expiratory flow rates of the patient.

The invention also provides a method of ventilating a patient in respiratory failure. In a preferred aspect, an RTC is inserted into the patient's trachea, and breathable gas is injected through the catheter to replace normal inspiration of the patient. This gas can be mixed with one or more other treatment gases, such as an anesthetic gas and/or nitric oxide, to facilitate additional functionality suitable for use, for example, in the ICU. Preferably, the step of mixing is accomplished by controlling a solenoid by the microprocessor.

Alternatively, an endotracheal tube ("ETT"), known by those skilled in the art, is used without an RTC. In this aspect, the invention provides other methods and modes of treating patients with respiratory failure. A pneumatic subsystem injects and controls breathable gas through the ETT to replace and/or augment the normal inspiration of the patient. As above, this gas is typically humidified and can be controlled and mixed with other treatment gases, as desired, by the attending physician.

In still another aspect, the invention provides a portable ventilator, including a pneumatic subsystem with a reverse thrust catheter, one or more sensors, and one or more actuators connected to a microprocessor subsystem. The microprocessor subsystem is connected to receive information from the sensor and to control the actuator. The microprocessor subsystem can also select one or more ventilation modes that control the pneumatic subsystem in a manner corresponding to the mode. The microprocessor subsystem further controls the actuator in response to signals generated from the sensor to vary one or more of (i) an inspiratory-to-expiratory ratio, (ii) a respiratory rate, and (iii) an intratracheal pulmonary flow to reduce carinal pressures of a patient.

In other aspects, the microprocessor subsystem includes memory and logic to store the signals for subsequent review by a user of the ventilator. Similarly, the microprocessor subsystem can display the signals for concurrent review by the user.

In a preferred aspect, the ventilator can operate selectively in one or more conventional modes, as needed and selected by the user, including but not limited to: (i) assist control mode ventilation (ACMV), (ii) synchronized intermittent mandatory ventilation (SIMV), (iii) continuous positive airway pressure (CPAP), (iv) pressure-control ventilation (PCV), (v) pressure support ventilation (PSV), (vi) proportional assist ventilation (PAV), and (vii) volume assured pressure support (VAPS).

In yet another aspect, the ventilator of the invention monitors selected patient information such as physiological trends, compositions, flow rates, pressures, volumes, and dynamic compliance data. In certain instances, the ventilator—through operation of the microprocessor—notifies the user that the information corresponds to a preselected value. By way of example, if one data variable under ventilator control exceeds a specified value, the ventilator can warn the user through a visual or tactile device, e.g., a light emitting diode (LED), to thereby enhance the safety of the patient. In addition, the microprocessor is programmable to respond to the same information so that it automatically adjusts the actuator, as needed, to modify selected parameters.

In one aspect, the ventilator has a variable oscillation of ventilation to achieve breathing rates between about 0 and 900 breaths per minute, and preferably above 120 breaths per minute.

The invention can also include a flow and oxygen control subsection to regulate incoming gas flow, oxygen concentration, and humidity, as needed, in a feedback loop with the patient's expiration.

In still another aspect, the invention provides a multifunction microprocessor-driven ventilator to support respiratory functions for an ill patient during any of the following activities: (a) ground or air transportation of the patient from the field or injury location; (b) travel to, or therapy within, an intensive care unit (hereinafter "ICU") and in multiple modalities; travel to an operating room (hereinafter "OR"); and support within OR for processes such as involving anesthesia. The microprocessor provides accurate and flexible control, for example, of air flow, pressures, and the concentrations of gases; and further enables real time variation of (i) inspired oxygen concentration ($FiO_2$), (ii) respiratory rates to between about 0 and 15 Hz, and (iii) the I:E ratio.

The invention thus provides several advantages. First, as a ventilator, the invention can provide many if not all of the respiratory support functions that a severely ill patient might need, from transport from the field to intensive care, to the operating room, and even as support through discharge from the hospital. Accordingly, as a single unit, the invention has flexibility to replace a multitude of existing prior-art clinical ventilator devices that are used successively during one patient's encounter or stay with the associated hospital. The computer or microprocessor control of the invention provides flexibility so far unavailable in existing ventilators, so as to provide, for example, continuous capture of patient data for "real-time" read out or storage for future clinical or research use. The invention also provides for continuous and "real time" monitoring of relevant patient data, e.g., physiological trends, compositions, flows, pressures, volumes, and dynamic compliance data; and responds or notifies the user or connected facility of user-selected warnings, e.g., a warning buzzer, alarm or light, when a selected data characteristic is met. Further, the invention can be used for both state-of-the-an and experimental functions, including, but not limited to: high frequency ventilation, i.e., oscillation; nitric oxide administration; mobile transport ventilation; OR ventilation such as for functioning as an anesthesia machine; ITPV; and conventional ventilation with both pressure and volume modes.

In a preferred aspect, the invention provides a failsafe mechanism that converts the system to operate like a CMV if the ITPV control circuitry fails or registers an undesirable signal. The failsafe mechanism can include, for example, an off-line power source that supplies energy to the system in the event of a power failure.

The invention also provides capability that is presently unavailable in prior art ITPV. In particular, in the prior art, ITPV is limited to 120 breaths per minute for peak respiratory rates, without warnings, and are further limited in the selectable options of I:E ratios. The invention, through precise control of the various pneumatic functions, permits ITPV rates of 0–900 breaths per minute; and a near unlimited range of I:E ratios. Ventilators for CMV, on the other hand, typically have a limited number of preset I:E options. Experimentation has shown that small fragile lungs are very sensitive to I:E ratios; and thus a wider range of choices as provided by the invention is advantageous.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which.

DETAILED DESCRIPTION OF PREFERRED EMBODIMENTS

Figure 1A:
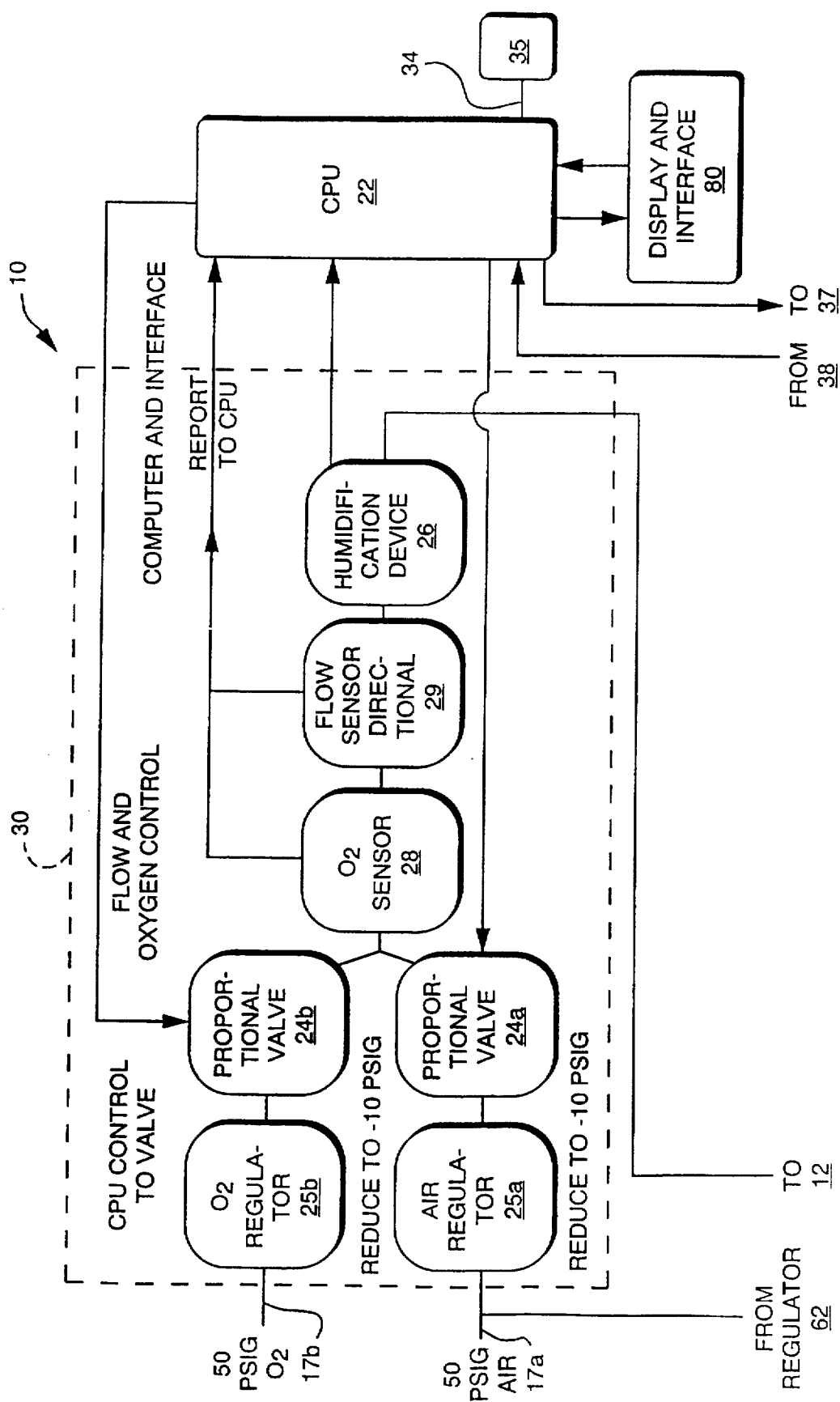
FIG. 1 illustrates a schematic layout of a system constructed according to the invention.
Figure 1B:
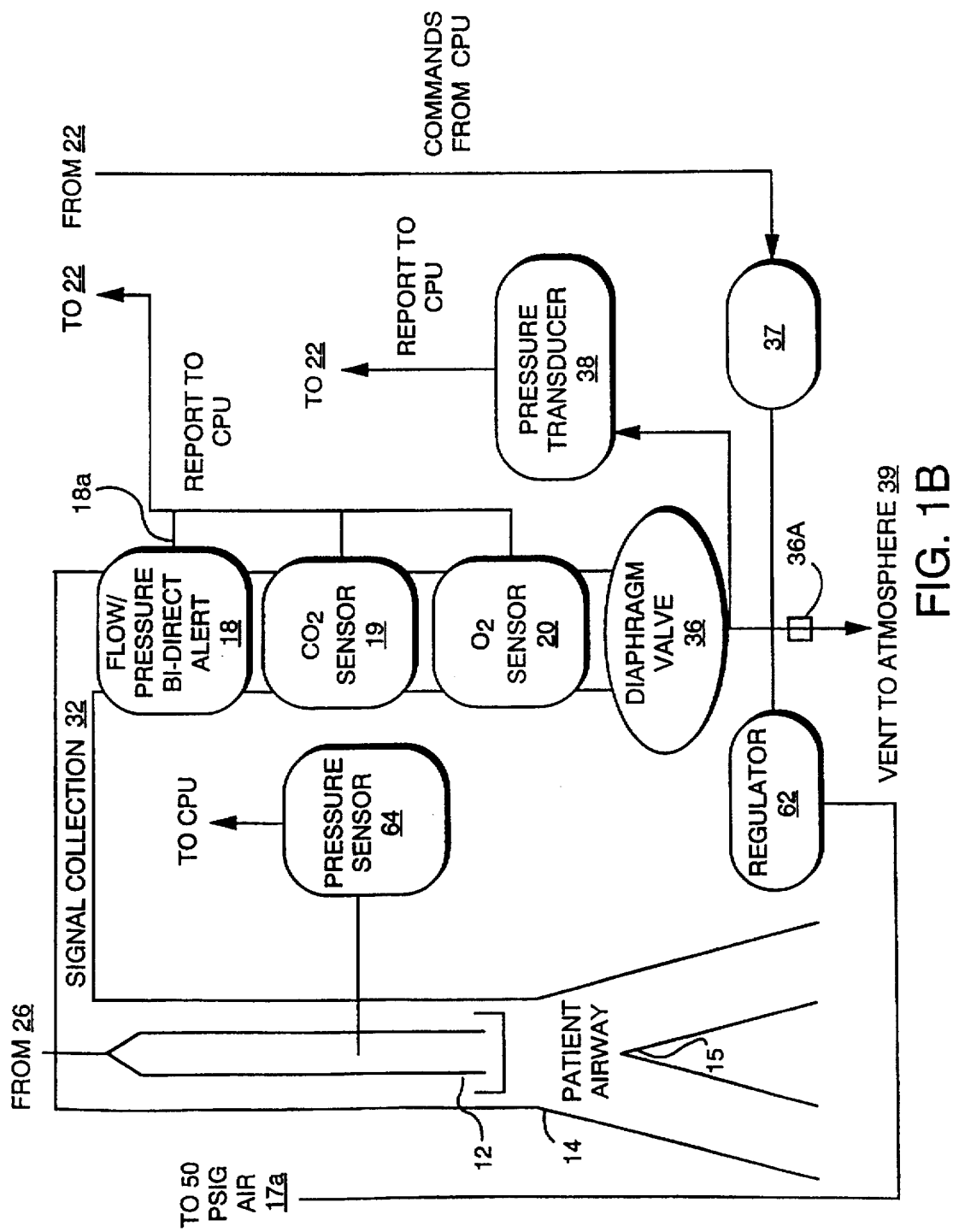

FIG. 1 illustrates a functional block diagram and schematic layout of a system 10 constructed according to the invention. The patient insert 12 depends upon the mode of operation. In ITPV operation, for example, the insert 12 includes an RTC; while in other modes, the insert 12 can be an ETT alone. The insert 12 is disposed within the patient's trachea 14, near to the carina 15, and pressurewise connected to (i) the gas and $O_2$ sources 17A, 17B, respectively, and to (ii) readout sensors 18-20 described in more detail below.

The central processing unit 22 ("CPU," "microprocessor," or computer) provides overall control of the system 10 to accurately specify the characteristics of the patient's breathing. Accordingly, the system 10 of the invention includes a feedback loop whereby the CPU 22 monitors events and characteristics of the patient's breathing, and controls selected actuators to modify such events and characteristics in near real time. By way of example, the CPU 22 controls both proportional valves 24A, 24B so as to control and regulate the flow of gas and $O_2$, respectively, through the air and $O_2$ regulators 25A, 25B in response to signals from the flow sensor directional 29 and the oxygen sensor 28. In another example, the oxygen sensor 28 and the flow sensor directional 29 also communicate with the CPU 22 to provide important information about the flow rate and oxygen content of the incoming gases.

Sensors 28, 29 and device 26 are part of the flow and oxygen control section 30 which operates to ensure that desirable and/or selected humidified air, with fresh oxygen, is injected to the patient's carina so as to replace or augment the patient's normal inspiration (in ITPV mode, for example, substantially all inspiration is replaced with computer-controlled inspiration and gas injection). If, for example, the flow sensor 29 signaled to the CPU 22 that the flow had changed from the operator-selected level, then the CPU 22 would adjust proportional valves 24a, 24b to make the requisite correction.

The same is true of flow/pressure bidirection alert sensor 18 of the signal collection section 32. That is, should the sensor 18 detect an incorrect flow and/or an undesirable pressure, it alerts the CPU 22 through signal line 18A to readjust the flow. A corresponding alert can thereafter be sent by the CPU 22 to a user of the system 10 via signal line 34 connected to an alert device 35, e.g., a LED, buzzer or tactile device.

In the pneumatic subsystem, described in more detail below in connection with FIGS. 2 and 3, the diaphragm valve 36 operates as a valve between the collection section 32, the inlet source 17a, and the outside world. More particularly, diaphragm valve 36 is controlled by RATE solenoid 37. Valve 36 is in fluid communication with pressure transducer 38 so that the CPU 22 can command cyclical operation of the solenoid to correspond to the patient's expected or desired expiration. Inspiration and expiration are thus controlled by the RATE solenoid 37: inspiration occurs when the solenoid 37 is active; and expiration occurs when the solenoid 37 is inactive.

Fixed leak 36a provides a vent to the outside ambient pressure 39; while regulator 62 provides step down regulation of gas pressure from the source 17a. The transducer 38, on the other hand, supplies critical pressure information to the CPU 22 so that the expiration pressure can be monitored and/or recorded by the CPU 22.

Preferably, a pressure sensor 64 resides within or near to the catheter 12 so as to provide localized pressure information to the CPU 22.

The information collected and controlled by the system 10 is both viewed and defined at the display and interface section 80. At this interface, a user can select the desired ventilatory mode, e.g., CPAP, and select certain other feedback features to be controlled automatically by CPU 22. The section 80 can further provide a visual or audible alert to the user in response to a determination by CPU 22 that a certain ventilatory characteristic has reached or exceeded some specified or nominal value.

Experimental Results

Three lambs, each between six and seven kilograms, underwent cesarean section and tracheotomy to facilitate placement of arterial and venous lines. All protocols were in conformance with Massachusetts General Hospital's Subcommittee on Research Animal Care and with the guidelines of the National Institute of Health ("NIH"). The lambs were initially supported by a CMV system and were allowed to reach steady-state to acquire measurements of baseline vital signs, arterial blood gases, and ventilatory settings. The anesthetized lambs were then connected to a pulmonary ventilator system constructed according to the invention and ITPV was instituted at a rate of one hundred breaths per minute. The ITPV flow was adjusted to achieve lower peak carnal pressures than obtainable in conventional ventilation. In a stepwise fashion, respiratory rate, I:E ratio, and ITPV flows were then varied while maintaining constant $PaCO_2$. In addition to the data collected by the microprocessor, serial vital signs and arterial blood gases were recorded. Statistical analysis was thereafter performed using the paired t-test, with $p<0.05$ considered significant. Similar experiments were repeated in six preterm lambs, each between 1.8 and 3.6 kilograms.

The testing results between a CMV system and an ITPV system constructed according to the invention are as follows (both systems were set to a rate of 100 and an I:E ratio of 1:3): the gas exchange was maintained despite a drop in average peak carinal pressure for the newborn lambs from 18.3 cm H$_2$O on CMV to 10.3 cm H$_2$O on ITPV (p=0.028). The average peak pressure fell even further at higher ITPV rates with adjustments in the I:E ratio. For the premature lambs, peak carinal pressures also fell significantly on ITPV (44 to 32 cm H$_2$O, p=0.002) with a corresponding significant improvement in ventilation (PaCO$_2$ from 52.2 to 31.9 mm Hg, p=0.029).

The experimental results show that the ITPV system of the invention operates at rates and I:E ratios previously unobtainable by prior art systems. In newborn and premature lambs, for example, the ITPV functioned most effectively with higher gas flow rates and with longer exhalation, providing improved gas exchange at lower peak carinal pressures. Accordingly, ITPV is particularly beneficial in achieving gas exchange in newborns while avoiding barotrauma, thus facilitating ventilation in newborns with CDH or prematurity to improve gas exchange and reduce barotrauma in the neonatal ICU.

Figure 2:
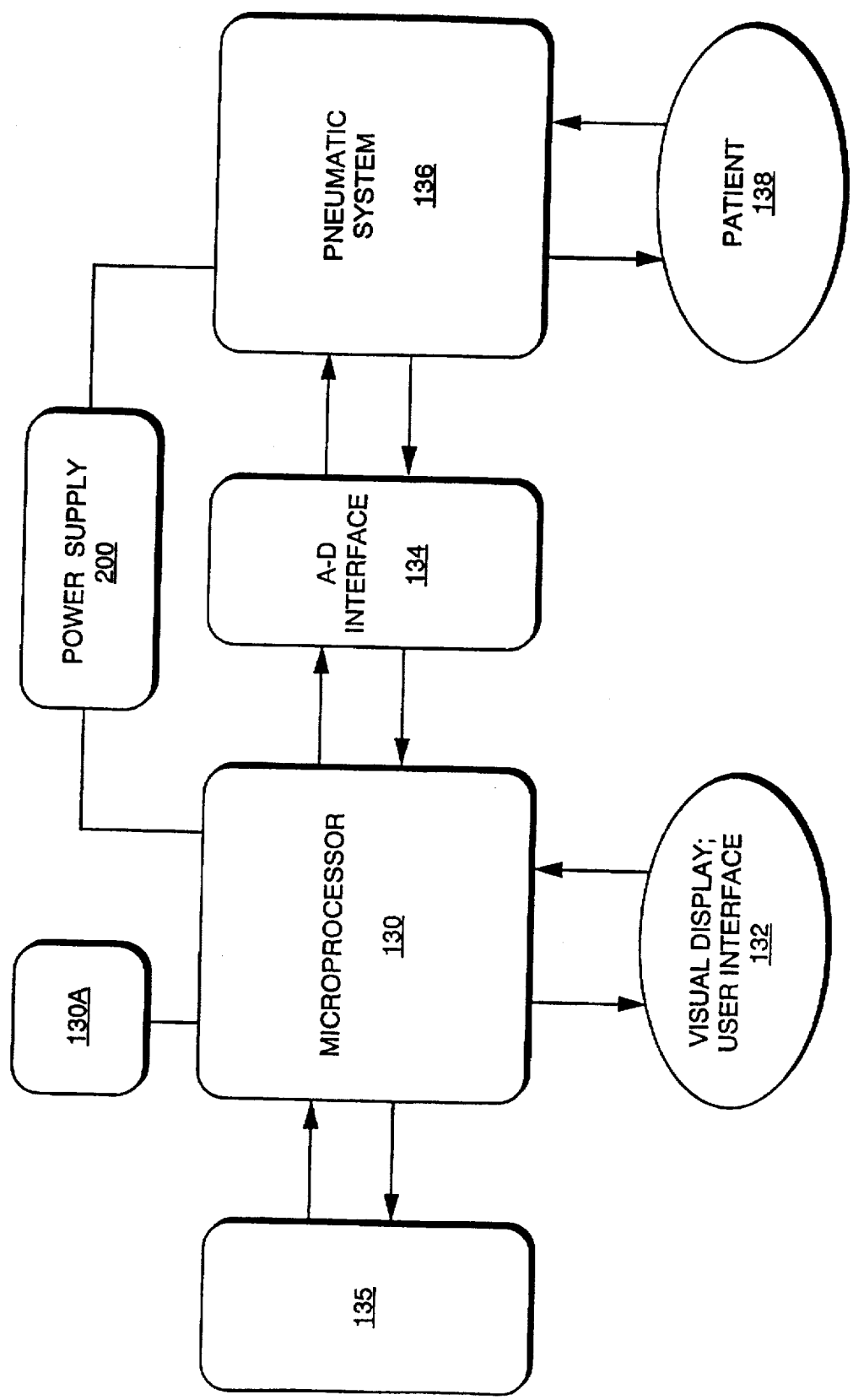
FIG. 2 illustrates a functional block diagram of a pulmonary ventilator ITPV system constructed according to the invention.
Figure 3:
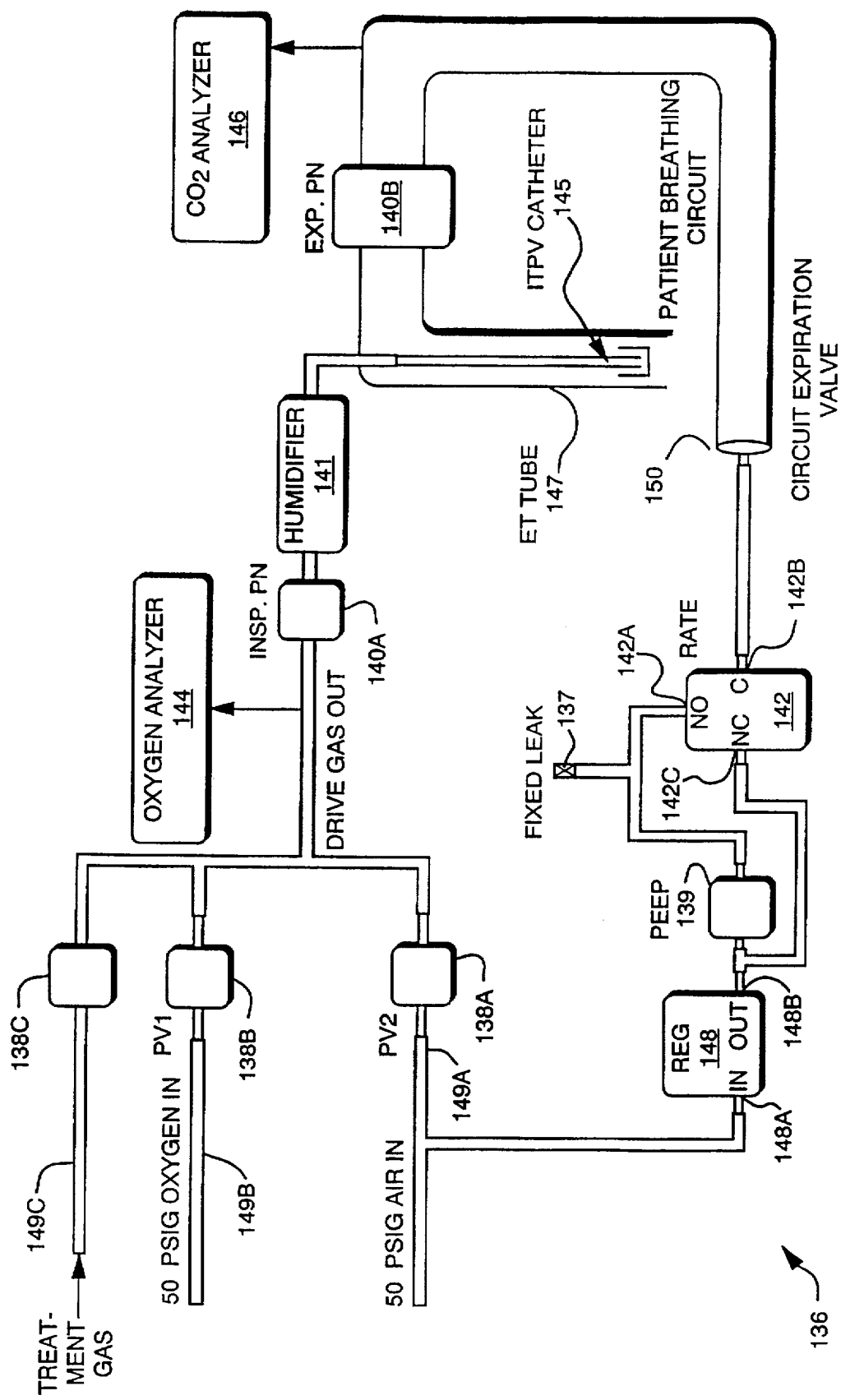
FIG. 3 shows greater detail and a functional schematic of a pneumatic circuit subsystem constructed according to the invention.

FIGS. 2 and 3 show greater detail of a ventilator system constructed according to the invention. Such a system is particularly useful in controlling ITPV, regulation of gas flow rates, oxygen concentrations, cycle (respiratory rate), and peak end expiratory pressure ("PEEP"). Specifically, FIG. 2 illustrates a microprocessor 130 connected to a visual display and user interface 132 for user-defined control of the pneumatic subsystem 136 and visual display of selected data returned from the subsystem 136. By way of example, microprocessor 130 and interface 132 can be in the form of the computer which houses specially designed software within internal memory.

The A–D interface 134 provides analog-to-digital conversion between the microprocessor 130 and the pneumatic subsystem 136. The subsystem 136 is connected for fluid communication with the patient 138, for example, through pneumatic tubing (e.g., an ETT) and an RTC (not shown). Specifically, the A–D converter 134 collects all signals from sensors in the subsystem 136, e.g., the sensors 18–20 of FIG. 1, and outputs commands from the microprocessor 130 to control the operation of the subsystem 136, thereby controlling the patient's breathing. In this way, the microprocessor 130 interprets all incoming information from the patient 138, performs parameter calculations, and sends commands to the pneumatic circuit subsystem 136 to make necessary adjustments that affect the patient 138.

The pneumatic subsystem 136, shown in more detail in FIG. 3, receives commands from the microprocessor 130 and performs the required ventilatory functions as described herein. Subsystem 136 also senses and measures certain parameters, such as gas flow rate, and relays the associated analog information to the A–D converter 134 so that the microprocessor 130 can process and act on a digital representation of this information. In turn, the microprocessor 130 commands various ventilatory changes to the subsystem 136, if needed, to control or otherwise modify the breathing characteristics of the patient. These control signals are similarly converted to analog signals, such as a voltage vs. time signal, by the converter 134 which proportionally controls the various valves in the subsystem 136.

The subsystem 136 contains the following units, each of which has an associated function: differential pressure proportional solenoid valves 138A, 138B control the overall flowrate and percentages of oxygen and air, respectively, flowing into the system 136; flow sensor pneumotachs 140A, 140B quantify, respectively, inspiratory and expiratory flow rates; proportional solenoid 139 provides the output of PEEP to feed the NO ("normally open") port 142a of the 3-way RATE solenoid 142; RATE solenoid 142 further controls respiratory rate by inflating the expiration valve balloon 150 (e.g., to 150 cm H$_2$O), thereby blocking circuit flow to momentarily cause an increase in circuit pressure to deliver an inspiratory breath.

Rate is controlled by periodically inflating and then deflating the common expiration valve 150. Air, typically at a pressure of 50 PSIG, is fed into the input 148a of a step down regulator 148. The regulator 148 is generally preset for 150 cm H$_2$O, corresponding to a maximum of allowed system pressure and expiratory valve levels). The output 148b of the regulator 148 feeds the PEEP proportional solenoid 139 and the RATE solenoid 142.

System PEEP is maintained by the PEEP solenoid 139 and a fixed leak 137. When the RATE solenoid is inactive, i.e., when the NC ("normally closed") port 142c is closed, the output of PEEP is fed through the NO and C ports, 142a, 142b, respectively. The fixed leak 137 provides bleed-down and pressure equalization in the PEEP circuit and relative to the expiration valve 150. PEEP in the patient circuit thereby provides variable flow to the fixed leak to control pressure to that of the expiration balloon valve 150.

The humidifier 141 typically includes heaters for selective humidification of the flow into the system 136, e.g., through an ITPV catheter 145 such as the RTC, and into the patient's endotracheal tube 147. Oxygen and carbon dioxide sensors 144, 146, respectively, quantify key gases under control within the subsystem 136.

Gases are injected through any of a plurality of inputs, e.g., the air input 149A; oxygen input 149B, and treatment gas input 149C, and preferably through selected proportional valves 138A, 138B, 138C, respectively. In this way, a selected combination of gases, such as oxygen, air and an anesthetic gas, can be simultaneously or independently injected into the patient's endotracheal tube 147.

Each of the units of FIG. 3 are connected for control and/or monitoring by the microprocessor, e.g., the microprocessor 130 of FIG. 2. For example, pneumotachs 140A, 140B, PEEP solenoid 139, and sensors 144, 146 are each connected to provide information to the microprocessor. The humidifier 141, regulator 148, and valve 150 are responsive to the microprocessor so as to provide physical control of the parameters related to the patient's breathing, such as the I:E ratio.

With further reference to FIG. 2, on-line visual color display and interface 132 is provided for the user to monitor and control all activities associated with the subsystem 136. The feedback circuitry of the subsystem 136 with the microprocessor thus permits closed-loop control of rate, flow, oxygen concentration, circuit PEEP levels, and concentrations and flows of any other gases. These parameters are derived from the signals produced by the various sensors of FIG. 3. In the illustrated form of the invention, these signals are sampled, via the A–D converter 134, and stored in memory 135 at user-defined rates for as-needed retrieval and analysis. The memory 135 may be, for example, a floppy disk drive or internal RAM or hard drive of an associated computer. These patient data may be stored to provide a permanent log of all events related to the patient's course on the ventilator, and allow on-line and retrospective analysis of pulmonary function, i.e., compliance, and gas analysis as a function of time. Furthermore, the CPU 130 can perform operator-specific physiological calculations on-line and in real-time, such as the calculation of $V_D/V_T$, $CO_2$ production, and $O_2$ consumption. Alternatively, these data can be stored for later analysis and review.

The results of the testing described in connection with FIGS. 2 and 3 illustrate certain advantages of the invention over the prior art mechanical and ITPV ventilators. For example, the microprocessor control of the solenoid 142, FIG. 3, and the regulator 148 permit variable flow rates between about zero and fifteen hertz (Hz), i.e., 0 to 900 breaths per minute. Secondly, the invention can operate over a virtually unlimited range of inspiratory and expiratory I:E ratios, from 0.00 to 99.99:1 in increments of 0.01. The invention can further perform in multiple modalities within one unit, including ITPV, pressure control, volume control, and high frequency ventilation, and can include all the modalities of the prior art because of the flexibility and operative control of the pneumatic subsystem 136 by the microprocessor 130, FIG. 2. Finally, as illustrated by the mixing of $O_2$ and air at the inlets 149B, 149A, respectively, of FIG. 3, the invention can also mix and deliver multiple gases, thereby functioning as an anesthetic machine. That is, one other gaseous input line 149C can be input to the subsystem 136 to control the inspiration of anesthesia to the patient, such as through the microprocessor control of proportional valve 138C. Other gases, such as nitric oxide (NO), helium (He), $CO_2$, hypoxic gas mixtures, and diagnostic gases, can also be input to the subsystem 136 by adding a similar input line.

The invention also incorporates monitoring and alarm systems that trigger upon the occurrence of selected user-defined events. By way of example, FIG. 2 illustrates an alarm 130A, e.g., an LED, buzzer or other warning sound generator, that is connected for control by the microprocessor 130. Since the microprocessor 130 monitors selected patient signals through the subsystem 136, it can selectively trigger the alarm 130A as needed, to inform the user that an event has occurred, such as an overpressure event. The alarm 130A can also be triggered upon the occurrence of favorable vital signs, showing for example stability of a patient's ventilatory state.

An alarm such as alarm 130A can also be used to trigger certain failsafe mechanisms, such as the power supply 200, which can be activated to supply power to the microprocessor 130 and pneumatic subsystem 136 in the event of a power failure. By way of example, the alarm 130A will activate if an associated sensor, e.g., pneumotach 140B fails to operate due to mechanical failure or power failure. In such a case, the system will convert to a CMV via control of the microprocessor 130 but without the feedback of the several feedback sensors.

More specifically, feedback electronics in the invention normal allows the closed loop control of several parameters, e.g., rate, flow, oxygen concentration and circuit PEEP levels. The operator can set levels for each of these parameters, control the pneumatic subsystem, and further monitor any and all connected sensors for system and patient performance. In the event of a failure, the system can revert to a CMV mode, thereby greatly reducing the risk to the patient. The invention permits this transformation because of the flexibility of the microprocessor 130 and pneumatic subsystem 136.

Other Experimental Results

Figure 4:
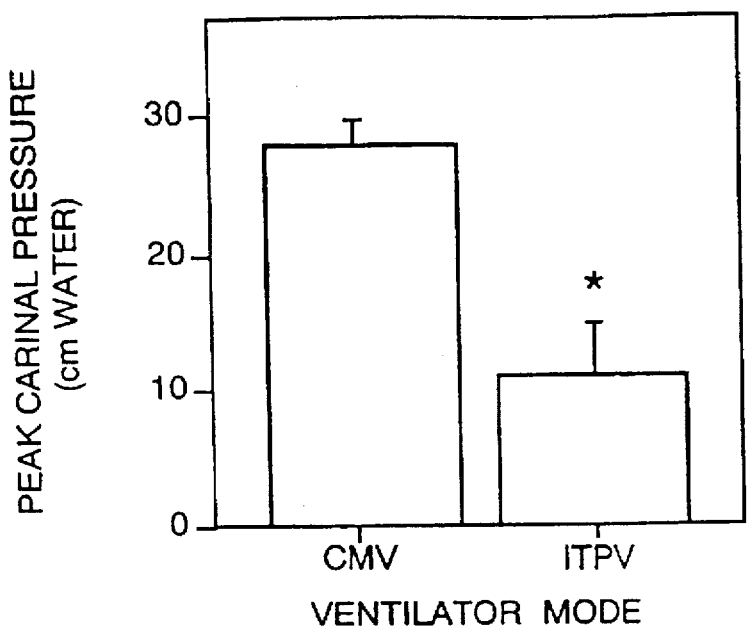
FIG. 4 shows measurement data of peak carinal pressures for term lambs on pressure-controlled CMV, operating at respiratory rates of 10-12 breaths per minute, and on ITPV instituted in accord with the invention, providing respiratory rates of up to 100 breaths per minute with a significant drop in peak carinal pressures (p=0.028)

During the testing of the several newborn lambs with the invention, the average peak carinal pressures dropped upon transition to ITPV while maintaining stable pH and $PaCO_2$. FIG. 4, for example, illustrates these results by showing that peak carinal pressure fell from 28 cm $H_2O$ on conventional ventilation to 10 cm $H_2O$ for ITPV (p=0.028) instituted according to the invention.

Figure 5:
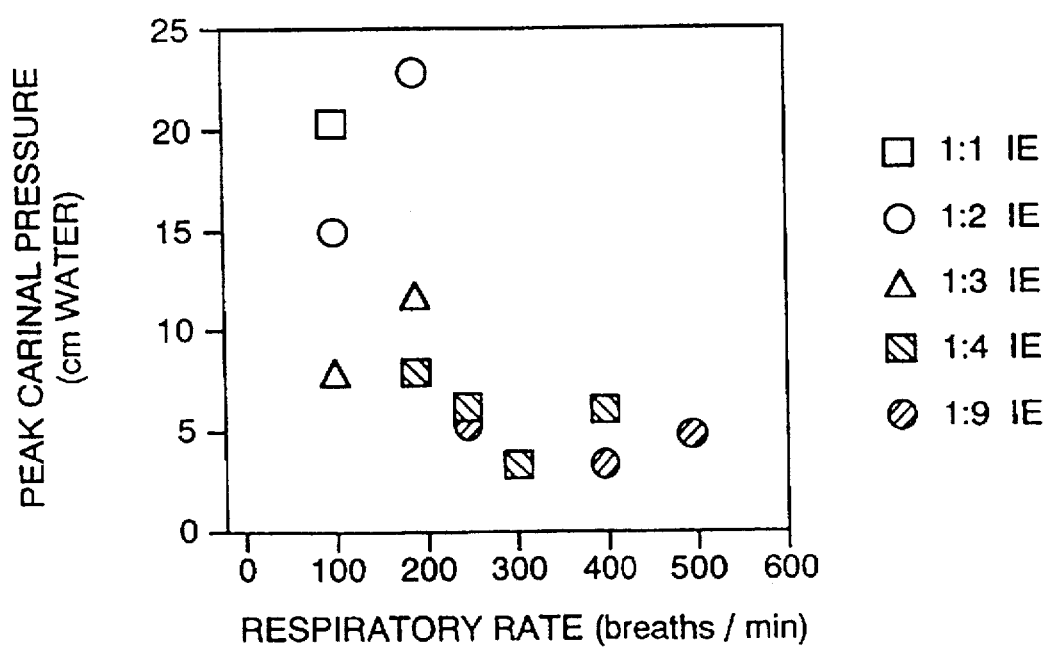
FIG. 5 shows measurement data of pressure versus respiratory rate in a term lamb for varying I:E ratios, in accord with the invention.

FIG. 5 illustrates the sensitivity of peak airway pressure to I:E ratios in a representative newborn lamb as measured by a system constructed according to the invention. The trends of FIG. 5 indicate that newborn and preterm lambs are similar. For a given respiratory rate, for example, as exhalation time increases, carinal pressures drop considerably. This trend is even more pronounced at higher rates where pressures increased dramatically due to breath stacking, unless the exhalation interval was lengthened.

Figure 6:
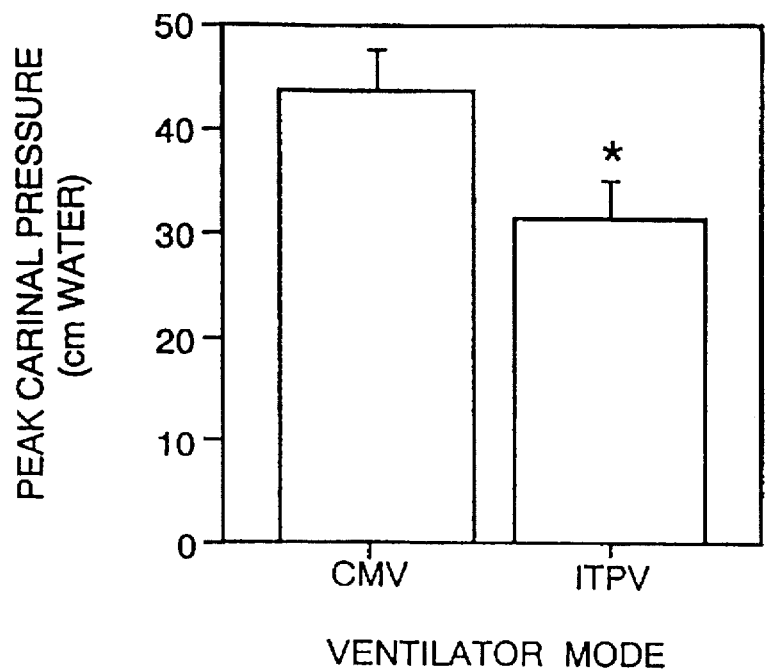
FIG. 6 shows measurement data of peak carinal pressures for preterm lambs on pressure-controlled CMV, respiratory rates of 50 breaths per minute, and ITPV instituted according to the invention, providing respiratory rates of between about 100-250 breaths per minute with a significant drop in peak carinal pressures (p=0.002)

In the preterm model, peak carinal pressures again dropped significantly upon transition to ITPV instituted according to the invention. FIG. 6, for example, illustrates that peak carinal pressure fell from 44 cm $H_2O$ on conventional ventilation to 32 cm $H_2O$ on ITPV (p=0.002) described herein.

Figure 7:
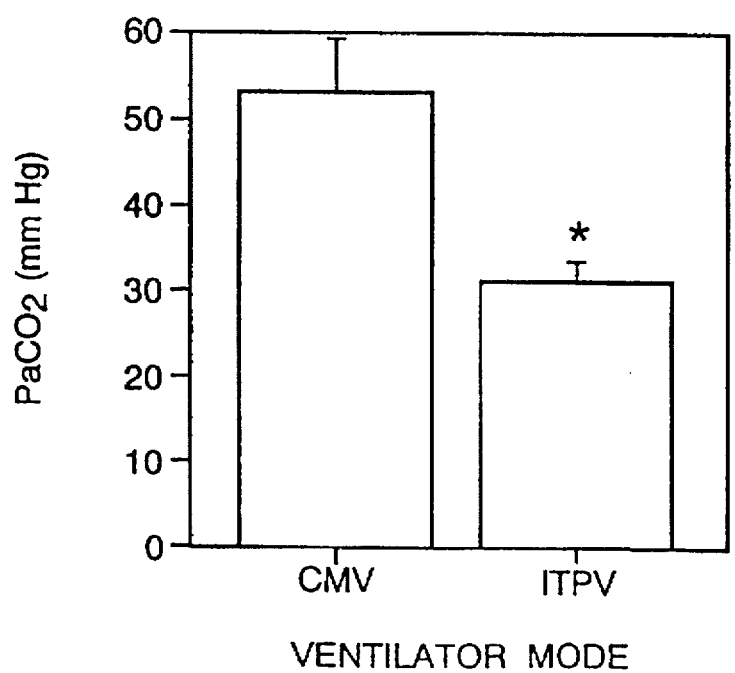
FIG. 7 shows measurement data of postductal arterial $PaCO_2$ for preterm lambs on pressure-controlled CMV and ITPV instituted according to the invention with a corresponding significant improvement in ventilation (p=0.029).

The invention also has improved ventilation of ITPV as compared to the prior art. FIG. 7, for example, illustrates that the postductal arterial $PaCO_2$ declined from 52 mm Hg on conventional ventilation to 32 mm Hg on ITPV (p=0.029) instituted according to the invention.

In larger animals, prior art research appeared to indicate that optimal I:E ratios are 1:1 on ITPV, with respiratory rates below 120 breaths per minute. However, as is now apparent through use of the invention, in smaller and immature lungs at higher rates, prolonged exhalation intervals are necessary, i.e., I:E ratios greater than 1:1. This augments the Venturi effect in the RTC and facilitates removal of gas from the lung while maintaining very low airway pressures. The sensitivity to I:E ratios may reflect a difference in the dynamics of small fragile airways. Accordingly, the invention provides the control and increase of the I:E ratio as needed to support the desired ventilatory characteristic.

The invention thus enhances the safety of ITPV in humans, for example, by monitoring selected features and eliminating the need for a separate ventilator, and by providing built-in safety features which reduce the likelihood of untoward events to the patient. The system of the invention is also portable and transportable so as to assist a patient's ventilation needs on the way to the hospital after the initial pick up. Because of the microprocessor-controlled flexibility, the hospital can keep the same mobile unit with the patient in the ICU, regardless of the required modes, thus providing a variety of desirable modes, including: ITPV, pressure control, volume control, continuous positive airway pressure, intermittent ventilation mode, and higher frequency ventilation.

In addition, the invention provides an improved ventilator which, unlike the prior art ITPV ventilators, optimizes gas exchange in newborns and at low airway pressures and higher frequencies. It further demonstrates an efficacy and improved ventilation at lower airway pressures in a prematurity model.

The invention thus attains the objects set forth above, among those apparent from the preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed as new and secured by Letters Patent is:

1. A ventilator system, comprising:
   A. a pneumatic subsystem for receiving one or more gases and for establishing a flow path to a patient insert at a distal end, B. at least one sensor, C. at least one actuator operatively coupled to the pneumatic subsystem; and D. a microprocessor subsystem connected to receive information from the sensor and to control the actuator, the microprocessor subsystem having means for selecting at least one ventilation mode and for controlling gas flow in the flow path of the pneumatic subsystem in a manner corresponding to the mode and for controlling the actuator in response to signals generated from the sensor to vary at least one of the group consisting of inspiratory-to-expiratory ratio (I:E), (ii) a respiratory rate and the I:E ratio, and (iii) an intratracheal pulmonary flow to establish predetermined carinal pressures in a patient.

2. A ventilator system according to claim 1, wherein the microprocessor subsystem further comprises means for storing the signals for subsequent review by a user of the ventilator system.

3. A ventilator system according to claim 1, wherein the microprocessor subsystem further comprises means for displaying the signals for concurrent review by a user of the ventilator system.

4. A ventilator system according to claim 1, wherein the means for selecting at least one ventilation mode further comprises means for selecting a plurality of modes selected from the group of (i) assist control mode ventilation (ACMV), (ii) synchronized intermittent mandatory ventilation (SIMV), (iii) continuous positive airway pressure (CPAP), (iv) pressure-control ventilation (PCV), (v) pressure support ventilation (PSV), (vi) proportional assist ventilation (PAV), (vii) volume assured pressure support (VAPS), and (viii) intratracheal pulmonary ventilation (ITPV).

5. A ventilator system according to claim 1, further comprising means for monitoring selected patient information including one or more of the following: physiological trends, compositions, flow rates, pressures, volumes, and dynamic compliance data.

6. A ventilator system according to claim 5, further comprising means for notifying a user of the ventilator system that the information corresponds to a preselected value.

7. A ventilator system according to claim 5, further comprising means for warning a user of the ventilator that the information corresponds to a preselected value, thereby providing enhanced safety for the patient.

8. A ventilator system according to claim 7, wherein the means for warning comprises one or more of an audible and visible alert.

9. A ventilator system according to claim 5, further comprising means for conveying a signal to the microprocessor indicating that the information corresponds to a preselected value, the microprocessor responding to the signal to automatically adjust the actuator.

10. A ventilator system according to claim 1, further comprising means for controlling I:E to be in the approximate range 0.00:1 to 99.99:1 in increments of about 0.01.

11. A ventilator system in accordance with claim 10, further comprising means for establishing respiratory rates in the approximate range 0–900 breaths per minute.

12. A ventilator system according to claim 11, further comprising means for establishing respiratory rates exceeding about 120 breaths per minute.

13. A ventilator system according to claim 1, further comprising a flow and oxygen control subsystem for regulating incoming gas flow, oxygen concentration, and humidity in said flow path of said pneumatic subsystem.

14. A ventilator system according to claim 1, wherein the patient insert comprises a reverse thrust catheter and wherein the pneumatic subsystem comprises means for providing substantially all of the patient's inspiration.

15. A ventilator system according to claim 1, wherein the patient insert comprises an endotracheal tube and wherein the pneumatic subsystem comprises means for operating a plurality of ventilating modes selectively.

16. A ventilator system according to claim 1, further comprising alarm means for informing a user of the system that a preselected event has occurred.

17. A ventilator system according to claim 1, further comprising alarm means for detecting an unsafe condition and failsafe means for operating the system as a CMV in the event the unsafe condition is detected.

18. A ventilator system according to claim 17, wherein the failsafe means comprises a power supply to provide power to the system in the event of power failure.

19. A method of controlling intratracheal pulmonary ventilation, comprising the steps of:

monitoring the inspiratory and expiratory flow rates of a patient during the ventilation to determine an I:E ratio; and controlling the flow rates to select an I:E ratio from about 0.00:1 to about 99.99:1.

20. A method according to claim 19, wherein the step of monitoring the flow rates comprises the step of monitoring the flow rates with a flow rate sensor connected to a microprocessor.

21. A method according to claim 19, wherein the step of controlling the flow rates comprises the step of regulating the flow rate from a microprocessor, the microprocessor being selectively responsive to a signal generated by a flow rate sensor connected in fluid communication with the patient.

22. A method according to claim 19, wherein the flow rate sensor is connected to sense the inspiratory flow rate of the patient.

23. A method according to claim 19, wherein the flow rate sensor is connected to sense the expiratory flow rate of the patient.

24. A method according to claim 19, further comprising the step of controlling the flow rates to maintain arterial $PaCO_2$ while lowering airway pressures.

25. A method according to claim 19, further comprising the step of controlling the flow rates to lower arterial $PaCO_2$ while maintaining a substantially constant airway pressure.

26. A method according to claim 19, further comprising the step of controlling the flow rates to achieve an I:E accuracy of about 0.01:1.

27. A method of ventilating a patient, comprising the steps of:

A. inserting a endotracheal tube whereby a distal tip of said tube is near the carina of the patient, B. inserting into the endotracheal tube a tube having a reverse thrust catheter at its distal tip, whereby the reverse thrust catheter is near the distal tip of the endotracheal tube, C. injecting breathable gas through the catheter to replace normal inspiration of the patient, D. controlling respiratory rates to be in the range 120–900 breaths per minute, E. controlling at least one of the group consisting of (i) I:E ratio, (ii) I:E. ratio and respiratory rate, and (iii) carinal pressures within a patient, and F. mixing the gas with one or more other treatment gases selected from the group of anesthesia, nitric oxide, helium, hypoxic gas mixtures, diagnostic gases, and mixes thereof.

28. A method according to claim 27 comprising the further step of controlling the inspiratory to expiratory ration (I:E) to be in the range of 0.00:1 to about 99.99:1 in increments of about 0.01:1.

29. A method according to claim 27 further comprising the step of mixing the gas with one or more other treatment gases.

30. A ventilator system according to claim 1, wherein the microprocessor subsystem further comprises means for continually flowing the gas in the flow path of the pneumatic subsystem, the gas flow being controlled by the microprocessor subsystem as a function of gas composition, flow rate and pressure.

31. A ventilator system according to claim 13, further comprising means for automatically regulating incoming gas flow, oxygen concentration, and humidity in said flow path.

32. A ventilator system, comprising:
a reverse thrust catheter of the type having a catheter tip and a gas conduit that diverts injected gas away from a patient's carina and tracheal walls;
control means connected to the catheter for adjusting at least one of the group consisting of (i) I:E ratio, (ii) I:E ratio and respiratory rate, and (iii) carinal pressures within a patient.

33. A ventilator system according to claim 32, wherein the control means comprises means for adjusting the I:E ratio to between about 0.00:1 and 99.99:1 selectively.

34. A ventilator system according to claim 32, wherein the control means comprises means for adjusting the respiratory rate to within the range of about 0–900 breaths per minute.

35. A ventilator system according to claim 32, wherein the control means comprises means for adjusting the respiratory rate to above about 120 breaths per minute.

* * * * *